US009861741B2

(12) United States Patent
Yang

(10) Patent No.: US 9,861,741 B2
(45) Date of Patent: Jan. 9, 2018

(54) TUBELESS FLUID DELIVERY DEVICE

(71) Applicant: MEDTRUM TECHNOLOGIES INC., Shanghai (CN)

(72) Inventor: Cuijun Yang, Shanghai (CN)

(73) Assignee: MEDTRUM TECHNOLOGIES INC., Shanghai (CN)

( * ) Notice: Subject to any disclaimer, the term of this patent is extended or adjusted under 35 U.S.C. 154(b) by 138 days.

(21) Appl. No.: 14/907,086

(22) PCT Filed: Mar. 25, 2014

(86) PCT No.: PCT/CN2014/073992
§ 371 (c)(1),
(2) Date: Jan. 22, 2016

(87) PCT Pub. No.: WO2015/106489
PCT Pub. Date: Jul. 23, 2015

(65) Prior Publication Data
US 2016/0158436 A1 Jun. 9, 2016

(30) Foreign Application Priority Data

Jan. 20, 2014 (CN) .......................... 2014 1 0025209

(51) Int. Cl.
*A61M 5/145* (2006.01)
*A61M 5/142* (2006.01)
(Continued)

(52) U.S. Cl.
CPC ...... *A61M 5/1452* (2013.01); *A61M 5/14248* (2013.01); *A61M 5/44* (2013.01);
(Continued)

(58) Field of Classification Search
CPC .. A61M 5/1452; A61M 5/14248; A61M 5/44; A61M 2005/14252;
(Continued)

(56) References Cited

U.S. PATENT DOCUMENTS 7,794,428 B2 9/2010 Estes et al.
2001/0053889 A1 12/2001 Marggi
(Continued)

FOREIGN PATENT DOCUMENTS

CN 101214399 A 7/2008
CN 201481927 U 5/2010
(Continued)

OTHER PUBLICATIONS

International Search Report for PCT/CN2014/073992, dated Sep. 29, 2014, ISA/CN.
(Continued)

*Primary Examiner* — Manuel Mendez
(74) *Attorney, Agent, or Firm* — U.S. Fairsky LLP; Yue Xu

(57) ABSTRACT

A tubeless fluid delivery device, comprising a controller (11) and a pump (12) combined with the controller (11). The controller (11) comprises a first housing having a first built-in circuit. The first housing is provided with a first engagement portion and a first insertion portion electrically connected to the first built-in circuit. The pump (12) comprises a second housing having a second built-in circuit, a drug storage cylinder, a piston, a push rod, a driving means and a battery. The second housing is provided with a second engagement portion correspondingly engaged with the first engagement portion and a second insertion portion electrically connected to the second built-in circuit. The second insertion portion is corresponding inserted in the first insertion portion to realize electrical connection. The present disclosure solves the problem that a drug fluid infusion device in the prior art has complex operation, large size and high cost.

19 Claims, 17 Drawing Sheets

(51) Int. Cl.
*A61M 5/44* (2006.01)
*F04B 17/03* (2006.01)
*F04B 19/22* (2006.01)
*F04B 23/02* (2006.01)
*F04B 53/14* (2006.01)
*F04B 53/16* (2006.01)
*A61M 5/172* (2006.01)

(52) U.S. Cl.
CPC .............. *F04B 17/03* (2013.01); *F04B 19/22* (2013.01); *F04B 23/02* (2013.01); *F04B 53/144* (2013.01); *F04B 53/16* (2013.01); *A61M 2005/14252* (2013.01); *A61M 2005/14268* (2013.01); *A61M 2005/1726* (2013.01); *A61M 2205/3569* (2013.01); *A61M 2205/36* (2013.01); *A61M 2205/3653* (2013.01); *A61M 2205/6054* (2013.01)

(58) Field of Classification Search
CPC ........... A61M 2005/14268; A61M 2005/1726; A61M 2205/3569; A61M 2205/36; A61M 2205/3653; A61M 2205/6054; F04B 17/03; F04B 19/22; F04B 23/02; F04B 53/144; F04B 53/16

USPC .............. 604/65–67, 151, 131; 128/DIG. 12, 128/DIG. 13
See application file for complete search history.

(56) References Cited

U.S. PATENT DOCUMENTS

2008/0243079 A1    10/2008   Wooley et al.
2008/0281297 A1    11/2008   Pesach et al.
2011/0009824 A1    1/2011    Yudfat
2011/0213306 A1    9/2011    Hanson et al.

FOREIGN PATENT DOCUMENTS

| CN | 202682463 U | 1/2013 |
| CN | 101528282 B | 3/2013 |
| CN | 203227106 U | 10/2013 |
| WO | 2009013735 A1 | 1/2009 |
| WO | 2011064780 A2 | 6/2011 |

OTHER PUBLICATIONS

English Translation of the 1st Office Action for CN201410025209.3, dated Jun. 28, 2017.
European search report dated Aug. 14, 2017.

TUBELESS FLUID DELIVERY DEVICE

CROSS-REFERENCE TO RELATED APPLICATIONS

The present application is a Section National Stage Application of International Application No. PCT/CN2014/073992, filed on Mar. 25, 2014, which claims priority to Chinese patent application No. 201410025209.3, filed on Jan. 20, 2014, and entitled "TUBELESS FLUID DELIVERY DEVICE", the entire disclosure of which is incorporated herein by reference.

TECHNICAL FIELD

The present disclosure generally relates to the field of medical appliance, and more particularly, to a tubeless fluid delivery device configured to continuously infuse fluid into a patient.

BACKGROUND

A fluid delivery device is a medical appliance which can achieve patient disease treatment by continuously infusing a drug into a patient. The fluid delivery device is widely used in the treatment of diabetes. The fluid delivery device continuously infuses insulin into a subcutaneous tissue of a patient based on a dosage required by the patient, so as to simulate the secretion function of the pancreas and to stabilize blood glucose of the patient. The fluid is usually stored in a pump base, and a conventional fluid delivery device usually infuses the fluid into a patient via a catheter/tube connected to the pump base. The catheter, when it is used, is an obstruction for the patient's activities. In order to overcome the above-mentioned shortcomings of the conventional fluid delivery device, a tubeless fluid delivery device has been developed, which has a pump base stuck to the patient's body by a medical adhesive tape. However, in the above-mentioned tubeless fluid delivery device, the pump base is integrated in a box with a controller, and the box is a disposable medical appliance. Such a tubeless fluid delivery device has high costs. Furthermore, the existing fluid delivery device also has some shortages such as complicated operation, large size, large mass, and inconvenient wearing.

When diabetes patients are being treated by insulin infusion, they usually need to wear two sets of components, one is a glucose probe and another is an insulin delivery system. A glucose sensor of the glucose probe and an indwelling cannula of the insulin delivery system are required to be inserted into and implanted into the subcutaneous tissue of the patients. Considering the comfort level of the patients when they are wearing these components, the two components are both made of slender and soft medical polymer materials. Because of the special natures of the materials and the shapes of the two components, they both need to be put into the subcutaneous tissue of the patients with a help of a puncture needle with a certain rigidity to puncture the skin of the patients. Thereafter, the needle is pulled out, leaving the two components in the subcutaneous tissue. The glucose sensor and the indwelling cannula have similar processes of puncture and indwelling, and similar mechanical structures for realizing these processes. Moreover, the glucose sensor and the indwelling cannula are also the same in aspects such as action area on body, disposable using, aseptic production, etc. Therefore, a concept of "two in one" is introduced in the present disclosure, leading to a micro system which integrates the glucose probe and the insulin delivery system in one body and has effects of both glucose monitoring and insulin administration.

SUMMARY

Regarding the above-mentioned shortcomings of the prior art, an object of the present disclosure is to provide a tubeless fluid delivery device for solving the problems of complicated operation, large size and high costs in the existing fluid delivery device.

In order to achieve the above-mentioned purposes and other related purposes, the present disclosure provides a tubeless fluid delivery device, including: a controller, including a first housing which has a first built-in circuit, where the first housing is provided with a first engagement part, and a first insertion part electrically connected to the first built-in circuit; and a pump base combined with the controller, which includes a second housing having a second built-in circuit, a reservoir, a piston, a push rod, a driving member and a battery, where the second housing is provided with a second engagement part correspondingly engaged with the first engagement part, and a second insertion part electrically connected to the second built-in circuit, where the second insertion part is correspondingly inserted in the first insertion part to realize electrical connection between the first built-in circuit and the second built-in circuit.

Optionally, the first engagement part is a clamping hole or a clamping slot. The second engagement part is a clamping hook corresponding to the clamping hole or the clamping slot, and the clamping hook is connected to a clamping hook handle which is used to disengage the clamping hook from the clamping hole or the clamping slot when needed. Or optionally, the second engagement part is a clamping hook corresponding to the clamping hole or the clamping slot, and the first housing is provided with a button used to disengage the clamping hook from the clamping hole or the clamping slot when needed.

Optionally, the first insertion part is a sealed socket. The sealed socket is provided with a groove in which a connector electrically connected to the first built-in circuit is provided, and an O-shaped sealing ring is set on a surface on which the connector is attached with the sealed socket. The second insertion part is a plug which includes a plug body circumferentially set with an O-shaped sealing ring, and a bolt embedded in the plug body. When the plug is inserted into the sealed socket, the bolt is inserted into the connector and electrically connected to the connector, and the O-shaped sealing ring on the plug body and the sealed socket fit tightly to achieve waterproof sealing.

Optionally, a main frame used as a supporter for the structure of the pump body and a supporter for the second built-in circuit is embedded in the pump body, and the second built-in circuit set on the main frame is a 3D printed circuit which is electrically connected to the second insertion part.

Optionally, a first combination of functions realized by signal lines on the second insertion part includes a position detection, a left in place detection, a right in place detection, a battery positive electrode, a blockage detection, a left side drive, a right side drive and a battery negative electrode; a second combination of functions realized by signal lines on the second insertion part includes a reference electrode, a buzz left in place detection, a public right in place detection, a battery positive electrode, a working electrode, a left side drive, a right side drive and a battery negative electrode; or a third combination of functions realized by signal lines on the second insertion part includes a position detection, a left in place detection, a right in place detection, a battery positive electrode, a buzz positive electrode, a left side drive, a right side drive and a battery negative electrode. Correspondingly, if the first combination or the second combination is used, a ground wire of the second insertion part is connected to a common port of the position detection, a common port of the left in place detection, a common port of the right in place detection, a common port of the blockage detection, and the battery negative electrode; if the third combination is used, the ground wire of the second insertion part is connected to the common port of the position detection, the common port of the left in place detection, the common port of the right in place detection, the common port of the blockage detection, the buzz positive electrode, and the battery negative electrode.

Optionally, the battery of the tubeless fluid delivery device is a button battery.

Optionally, the first built-in circuit of the controller includes a control circuit and a program processing module. The first housing is provided with a first buzzer chamber in which a first buzzer is disposed, and the first buzzer is connected to the first built-in circuit of the controller via a wire. Or the second housing is provided with a second buzzer chamber in which a second buzzer is disposed, and the second buzzer is connected to the second built-in circuit of the controller via a contact.

Optionally, the pump base further includes a subcutaneous cannula installation device having a steel needle, a steel needle bed, a spring and a toggle switch. The pump base further includes an indwelling cannula of the steel needle, and the indwelling cannula is implanted subcutaneously via the aid of the steel needle. If the steel needle is a hollow needle, the indwelling cannula covers the hollow needle; or if the steel needle is a groove steel needle, the indwelling cannula is set in the groove of the groove steel needle. A glucose sensor is set on the outer surface of the indwelling cannula.

Optionally, the pump base further includes a fluid outlet which is provided with an delivery fluid plug having a plastic base, a silica gel plug and a polymer film. The delivery fluid plug is connected to the second housing via a fastener, and the delivery fluid plug is detachable from the pump base when the plastic base is lifted.

Optionally, a medical adhesive tape configured to stick to the skin of a patient is fixed on the pump base.

Optionally, the tubeless fluid delivery device further includes a skin heating device configured to heat the skin at which the fluid is infused.

Optionally, the pump base further includes an identity recognition tag which may be a near field communication (NFC) tag, a radio frequency identification (RFID) tag or an identity recognition chip.

As mentioned above, the tubeless fluid delivery device in the present disclosure uses separable structure to reduce costs. Specifically, it defines the active controller as a main control machine, and defines the pump base as passive consumables. That is, the active part are taken as a reusable part, while the passive part is deemed as disposable. The two parts are packed separately and can be used together to complete the treatment of a patient. Specifically, when the tubeless fluid delivery device is used, the patient assembles the controller and pump base together to form the delivery device, sticks the tubeless fluid delivery device to his/her skin and then uses it as normal. When the fluid stored in the pump base runs out, or the device breaks down, the controller will remind the user, by using the buzzer, to remove and discard the pump base, and to install a new pump base and stick the tubeless fluid delivery device to the skin for sequential using.

Figure 1:
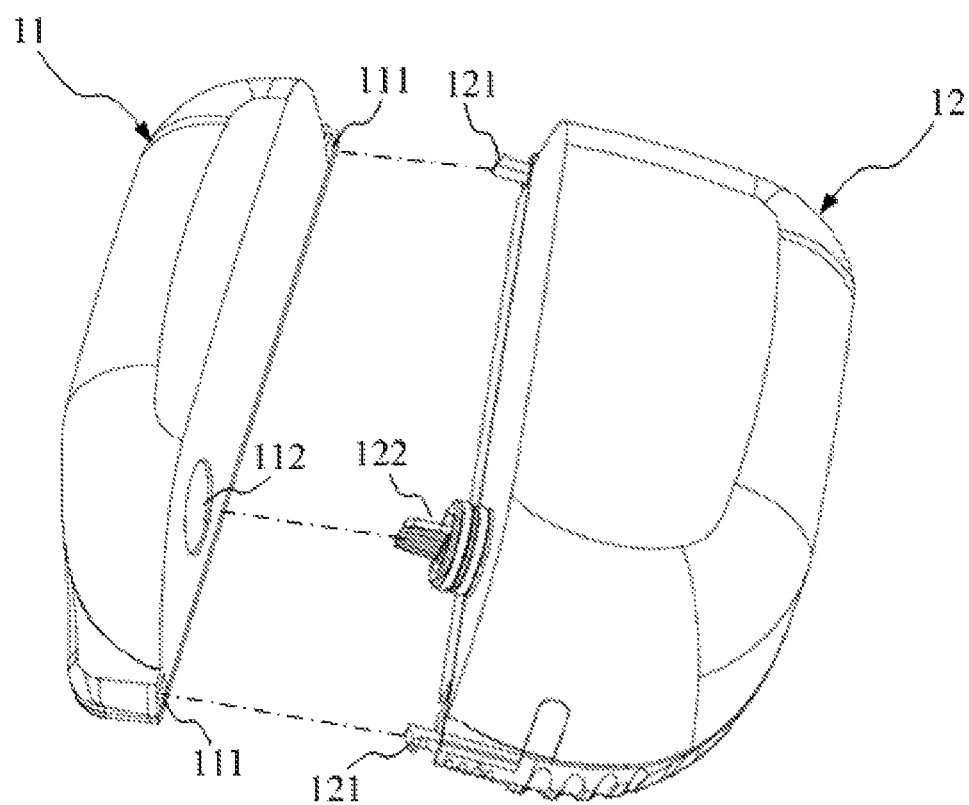
FIG. 1 schematically illustrates a tubeless fluid delivery device according to one embodiment of the present disclosure.

DESCRIPTION OF REFERENCE SIGNS 11 controller
111 first engagement part
1111 flange structure
112 first insertion part
1121 groove
113 first buzzer chamber
114 button
12 bump base 121 second engagement part
122 second insertion part
1221 plug body
1222 O-shaped sealing ring
1223 bolt
123 clamping hook handle
124 main frame
1241 ground wire
125 battery slot
1251 battery negative spring
1252 battery positive connector
1253 battery positive electrode
1254 conduction connector
126 slot for a reservoir
127 fluid outlet
1271 clamping hole
128 delivery fluid plug
1281 plastic base
1282 silica gel plug
1283 polymer film
1284 clamping hook
129 delivery fluid inlet
13 connector
131 O-shaped sealing ring
14 first buzzer and second buzzer
141 contact
15 button battery
16 subcutaneous cannula installation device
161 steel needle
162 steel needle bed
163 spring
164 toggle switch
165 auxiliary indwelling cannula
166 glucose sensor
17 medical adhesive tape
18 skin heating device
19 identity recognition tag

DETAILED DESCRIPTION OF THE DISCLOSURE

The embodiments of the present disclosure are described in the following through specific examples, and those skilled in the art can easily understand other advantages and effects of the present disclosure according to the content disclosed in the specification.

Referring to FIG. 1 to FIG. 20, it should be noted that, structures, scales and sizes shown in the drawings are only used to illustrate the contents disclosed in the specification, for being understood and read by those skilled in the art, instead of limiting implementation conditions of the present disclosure. Any modification in structure, change in scale, or adjustment in size should fall within the scope of the technical solution disclosed by the present disclosure without influencing the generated efficacy and achieved objective of the present disclosure. Meanwhile, some words such as "upper", "lower", "left", "right", "middle", and "a" quoted in the specification are only used for clarity of the illustration instead of limiting the implementation scope of the present disclosure, and any change or adjustment of relative relationships should be considered as falling within the scope of implementation of the present disclosure without essentially changing the technical content.

The present disclosure provides a tubeless fluid delivery device, which is configured to achieve patient disease treatment by continuously delivering a fluid into the patient. In practical application, the fluid delivery device can be widely used in treating of diabetes. The fluid delivery device continuously delivers insulin into a subcutaneous tissue of a patient based on a dosage required by the patient, so as to simulate the secretion function of the pancreas and stabilize blood glucose of the patient. The tubeless fluid delivery device in the present disclosure includes a controller and a pump base. The bump base is combined with the controller. Specifically, the pump base is mechanically combined with the controller by engaging a first engagement part and a second engagement part, and is electrically connected to the controller by connecting a first insertion part to a second insertion part.

The controller includes a first housing having a first built-in circuit, where the first housing is provided with a first engagement part and a first insertion part electrically connected to the first built-in circuit.

The pump base includes a second housing having a second built-in circuit, a reservoir, a piston, a push rod, a driving member and a battery, where the second housing is provided with a second engagement part correspondingly engaged with the first engagement part and a second insertion part electrically connected to the second built-in circuit, where the second insertion part is correspondingly inserted in the first insertion part to realize electrical connection between the first built-in circuit and the second built-in circuit.

Figure 2:
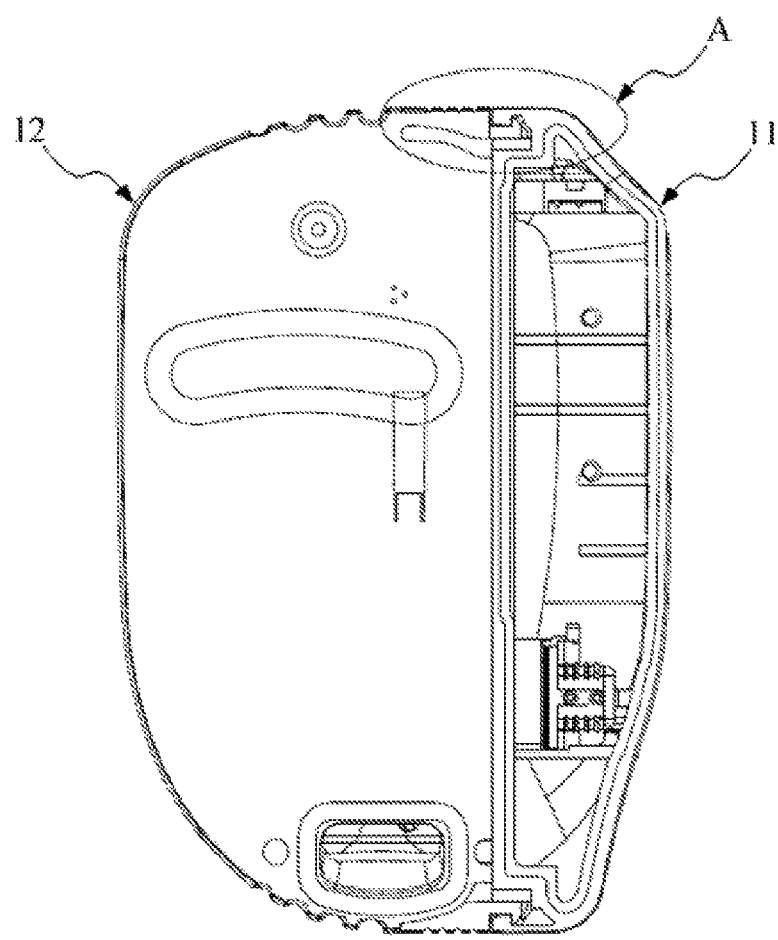
FIG. 2 schematically illustrates an operation structure according to one embodiment of the present disclosure.
Figure 3:
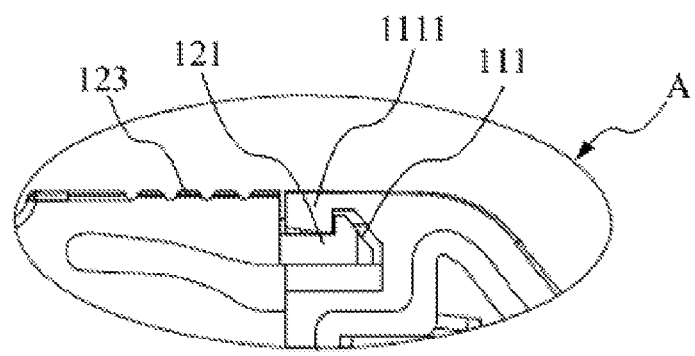
FIG. 3 illustrates an enlarged view in section A of FIG. 2.

Referring to FIG. 1, a tubeless fluid delivery device according to one embodiment of the present disclosure is schematically illustrated. As shown in FIG. 1, in the embodiment, the first engagement part 111 is a clamping hole. A flange structure 1111 is set inside the clamping hole, but it is not limited to this. The first engagement part 111 can also be a clamping slot or other structures that can be engaged with a clamping hook. Correspondingly, the second engagement part 121 is a clamping hook corresponding to the clamping hole, and the clamping hook is connected to a clamping hook handle 123. Referring to FIG. 2 and FIG. 3, FIG. 2 schematically illustrates an operation structure according to one embodiment of the present disclosure. FIG. 3 illustrates an enlarged view in section A of FIG. 2. As shown in FIG. 2 and FIG. 3, in some embodiments, the clamping hook can be disengaged from the clamping hole by controlling the clamping hook handle 123. Specifically, there is a gap between the inner side of the clamping hook handle 123 and the bottom shell of the pump base 12. When the clamping hook handle 123 is pressed, the clamping hook handle 123 pushed the clamping hook and disengages it from the clamping hole.

Figure 4:
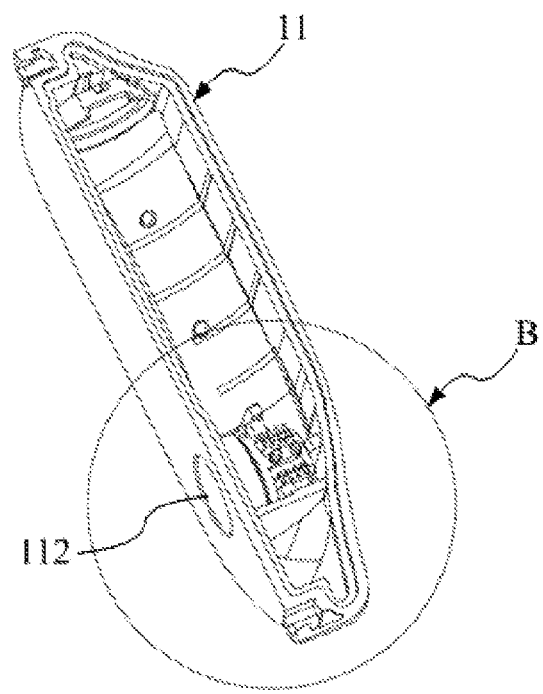
FIG. 4 schematically illustrates a first insertion part according to one embodiment of the present disclosure.
Figure 5:
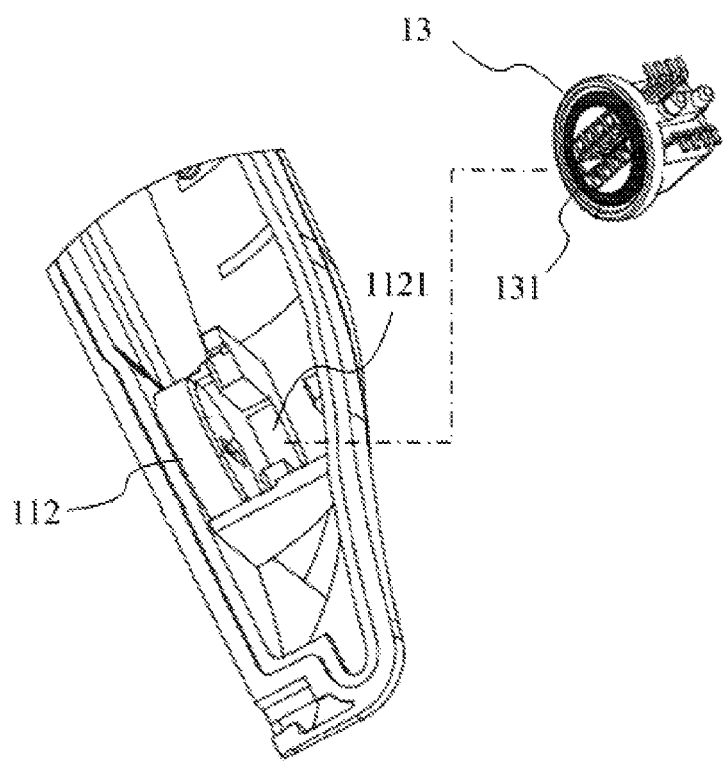
FIG. 5 illustrates an enlarged view in section B of FIG. 4.

In some embodiments, Referring to FIG. 4 and FIG. 5, FIG. 4 schematically illustrates a first insertion part according to one embodiment of the present disclosure. FIG. 5 illustrates an enlarged view in section B of FIG. 4. As shown in FIG. 4 and FIG. 5, the first insertion part 112 is a sealed socket. Specifically, the sealed socket is provided with a groove 1121, and the groove 1121 is provided with a connector 13 configured to be electrically connected to the first built-in circuit, where an O-shaped sealing ring 131 is set on a surface on which the connector 13 is attached with the sealed socket.

Figure 6:
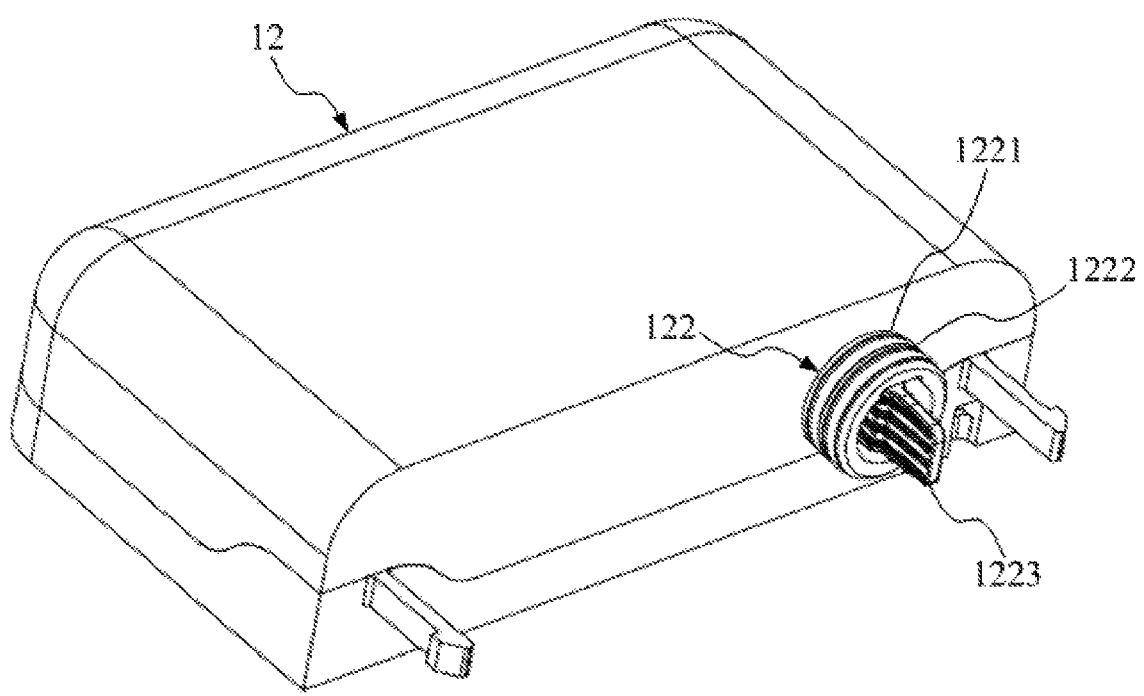
FIG. 6 schematically illustrates a second insertion part according to one embodiment of the present disclosure.

Correspondingly, the second insertion part is a plug. Referring to FIG. 6, a second insertion part according to one embodiment of the present disclosure is schematically illustrated. As shown in FIG. 6, the plug includes a plug body 1221 circumferentially set with an O-shaped sealing ring 1222, and a bolt 1223 embedded in the plug body 1221. The bolt 1223 is a wedge structure, which is convenient for the installation of the pump base. When the plug is inserted into the sealed socket, the bolt is inserted into the connector 13 and realizes electrical connection to the connector, where the O-shaped sealing ring 1222 on the plug body and the sealed socket fit tightly to achieve waterproof sealing.

In one embodiment, as shown in FIG. 6, the second housing of the pump base 12 includes a bottom shell of the pump base 12 and a top shell of the pump base 12. The bottom shell of the pump base 12 is provided with two clamping hooks and clamping hook handles 123, and the first housing of the controller 11 is provided with two corresponding clamping holes and the sealed socket. The connector 13 is set inside the sealed socket. When the pump base 12 and the controller 11 are combined, the clamping hooks are inserted into the clamping holes, and the plug is inserted into the sealed socket. The clamping hooks slide into the clamping holes guided by their front inclined plates and thus are engaged with the flange structures 1111 of the clamping holes. Therefore, the pump base 12 and the controller 11 are tightly combined together. Two O-shaped sealing rings 1222 on the plug body and the sealed socket are squeezed together to form a waterproof structure. There is a gap between the inner side of the clamping hook handle 123 and the bottom shell of the pump base 12. When the clamping hook handle 123 is pressed inwardly, the clamping hook handle 123 disengages the pump base 12 from the controller 11. From the above description, the pump base 12 and the controller 11 are combined by engaging the clamping hooks and the clamping holes, and realize electrical connection by inserting the plug into the sealed socket.

Figure 7:
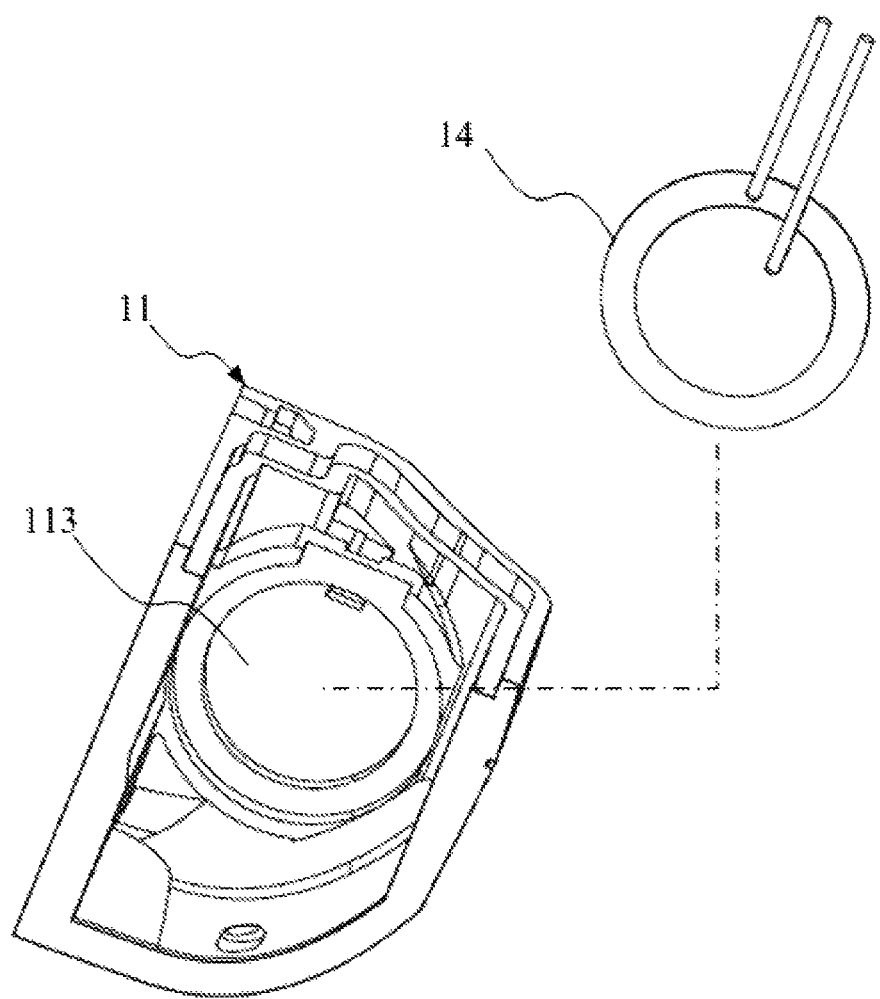
FIG. 7 schematically illustrates an exploded view of a first buzzer chamber and a first buzzer according to one embodiment of the present disclosure.
Figure 8:
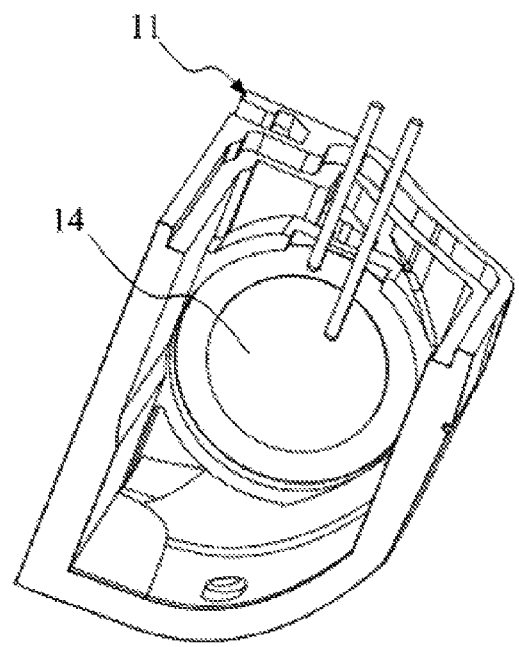
FIG. 8 schematically illustrates a combined view of a first buzzer chamber and a first buzzer according to one embodiment of the present disclosure.

Referring to FIG. 7 and FIG. 8, FIG. 7 schematically illustrates an exploded view of a first buzzer chamber and a first buzzer according to one embodiment of the present disclosure. FIG. 8 schematically illustrates a combined view of a first buzzer chamber and a first buzzer according to one embodiment of the present disclosure. As shown in FIG. 7 and FIG. 8, the first housing is provided with a first buzzer chamber 113, in which a first buzzer 14 is disposed, and the first buzzer 14 is connected to the first built-in circuit of the controller 11 via a wire (not shown). When the fluid stored in the pump base 12 runs out, or the device breaks down, the controller 11 will remind the user by using the first buzzer 14 to remove and discard the pump base 12, and to install a new pump base 12 and stick the tubeless fluid delivery device to the skin for sequential using.

Figure 9:
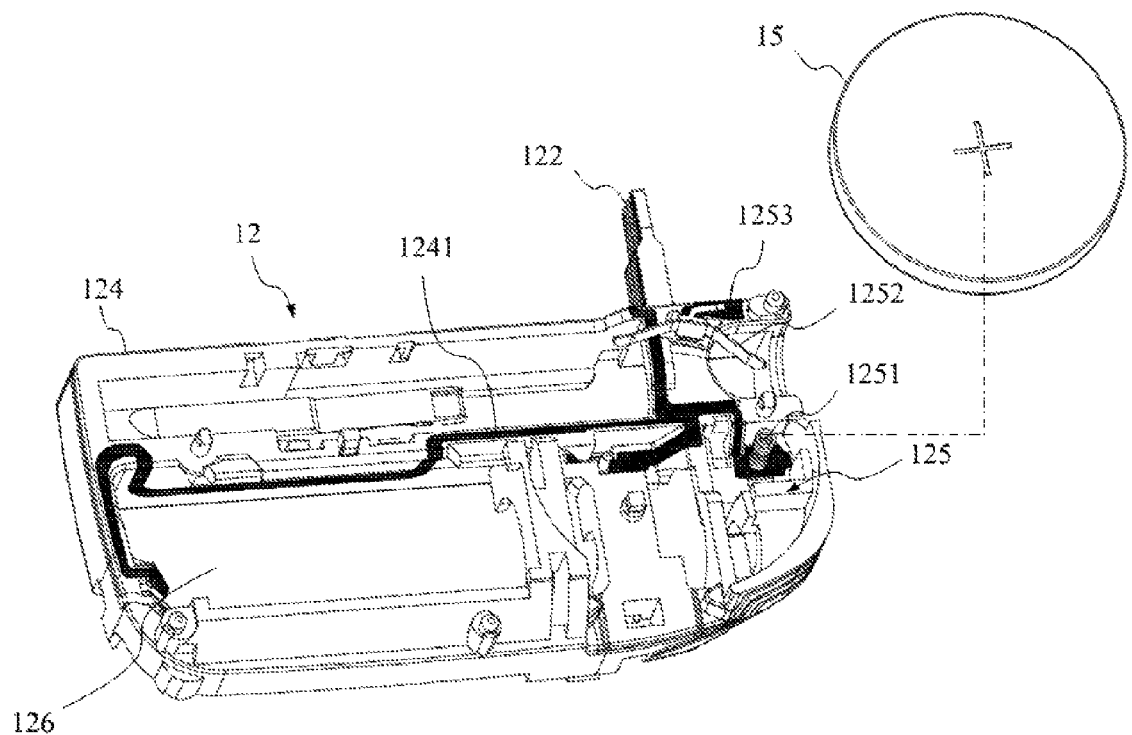
FIG. 9 schematically illustrates an exploded view of a structure with a battery according to one embodiment of the present disclosure.
Figure 10:
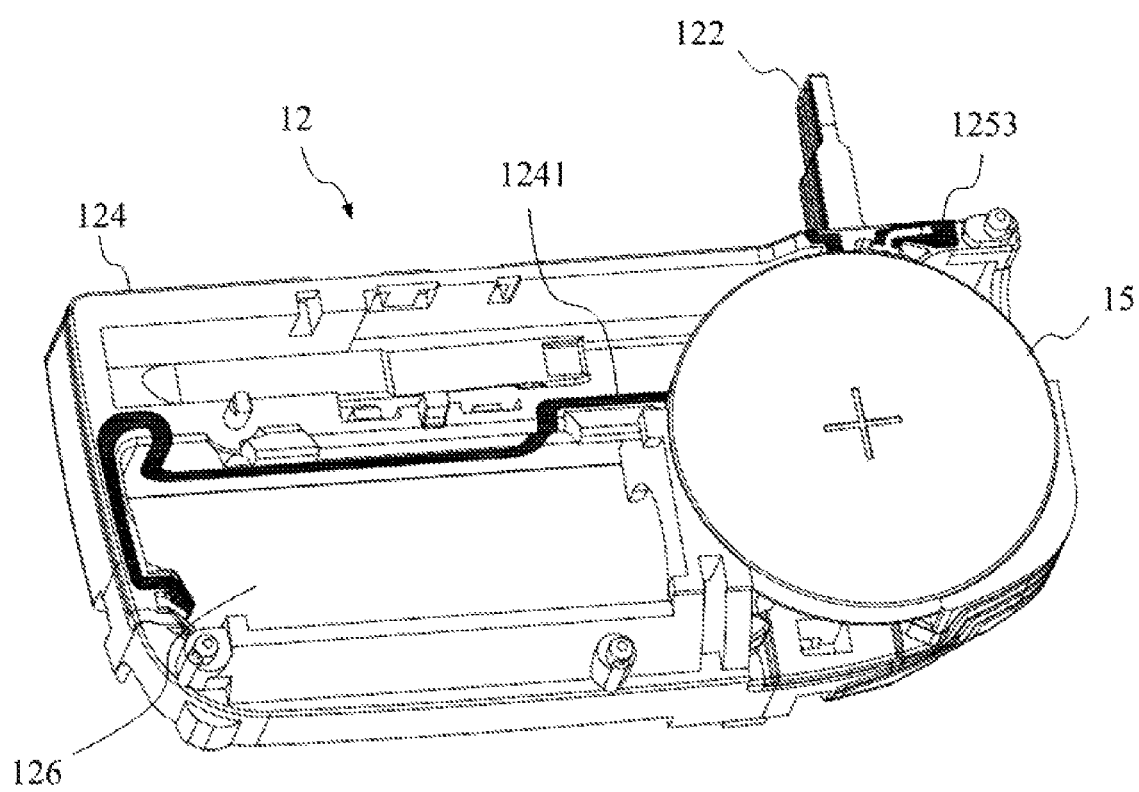
FIG. 10 schematically illustrates a combined view of a structure with a battery according to one embodiment of the present disclosure.

Referring to FIG. 9 and FIG. 10, an inner structure of the second housing according to one embodiment of the present disclosure is schematically illustrated. As shown in FIG. 9 and FIG. 10, a main frame 124 configured to be used as a structure supporter for the pump base and a supporter for the second built-in circuit is embedded in the pump body 12. The second built-in circuit set on the main frame 124 is a 3D printed circuit (not shown), which is electrically connected to the second insertion part 122. That is, the main frame 124 configured to be used as a structure supporter for the pump base and a supporter for the second built-in circuit is embedded in the pump body 12, and the main frame 124 is provide with a 3D printed circuit, which is electrically connected to the second insertion part 122, so that signal transmission from the connector 13 in the sealed socket of the controller 11 to the 3D printed circuit is realized. The second insertion part 122 is a plug which includes a plurality of signal lines. A first combination of function realized by the signal lines includes a position detection, a left in place detection, a right in place detection, a battery positive electrode, a blockage detection, a left side drive, a right side drive and a battery negative electrode. It should be noted that, in the figures according to the embodiment of the present disclosure, the signal lines is not given reference signs. That is, the arrangement of the signal lines is not limited to the above, other adjusted arrangements, including the signal lines according to the embodiment, also belong to the protection range of the present disclosure.

In one embodiment, as shown in FIG. 9 and FIG. 10, the main frame 124 configured to be used as a structure supporter for the pump base and the second built-in circuit supporter is embedded in the pump body 12. The main frame 124 has two important roles, one is to be used as a inserting supporter and a fixing supporter for all components of the pump base 12, the other is to support the 3D printed circuit through which the active controller 11 can control the pump base 12. The main frame 124 is manufactured by materials which can meet the temperature requirements of manual welding or even the high temperature welding of Surface Mount Technology (SMT). To prevent the interference between the shell of the pump base and the main frame 124 in the installing process, the main frame 124 is configured as a wedge structure. In the embodiment, the plug of the main frame 124 is configured as a bolt of the second insertion part 122. The signal lines are distributed on both sides of the plug of the main frame 124. The signal lines realize functions of position detection, left in place detection, right in place detection, battery positive electrode, blockage detection, left side drive, right left drive and battery negative electrode. Optionally, the signal lines near the side of the delivery fluid inlet successively realize function of blockage detection, left side drive, right left drive and battery negative electrode from top to bottom. And the signal lines in the other side successively realize function of position detection, left in place detection, right in place detection, and battery positive electrode.

The distribution of the main frame 124 and the ground wire in the pump base 12 are illustrated in FIG. 9 and FIG. 10. In one embodiment, the pump base 12 and the controller 11 are separated. The battery is a single button battery 15 and is set in battery slot 125 set on the main frame 124. The button battery 15 is fixed by the main frame 124 and a battery positive connector 1252. The battery positive connector 1252, a battery negative spring 1251 and the 3D printed circuit of the main frame 124 are coupled. The ground wire 1241 is connected to the common ports of position detection, left in place detection, right in place detection and blockage detection, and connected to the battery negative electrode.

In FIG. 9 and FIG. 10, the reference sign 126 indicates a slot for setting reservoir.

Figure 11:
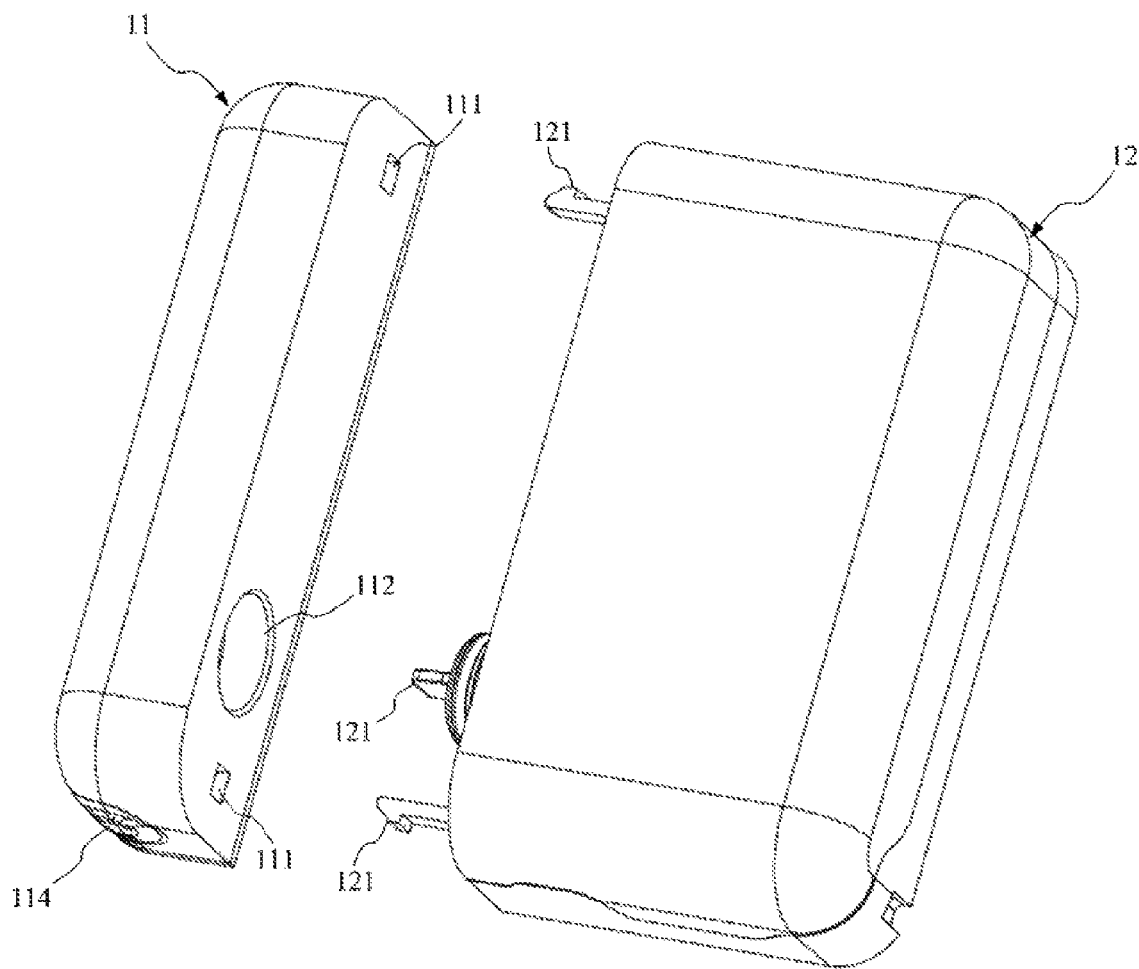
FIG. 11 schematically illustrates an operation structure according to another embodiment of the present disclosure.

Referring to FIG. 11, an operation structure according to another embodiment of the present disclosure is schematically illustrated. In the embodiment, the first housing of the controller 11 is provided with a button 114 configured to disengage the clamping hook from the clamping hole. Referring to FIG. 11, in the embodiment, the pump base 12 and the controller 11 are combined by the clamping hook set on the bottom shell of the pump base 12, and the controller 11 is provided with the button 114 configured to disengage the pump base 12 from the controller 11. The bottom shell of the pump base 12 is provided with two clamping hooks, and the controller 11 is provided with two buttons and the sealed socket in which the connector 13 is set. The top shell of the pump base 12 is provided with a plug. The plug of the main frame 124 penetrates through the gap of the plug set in the top shell of the pump base. The plug set in the top shell of the pump base and the plug of the main frame together form the plug of the pump base 12. When the pump base 12 and the controller 11 are combined, the clamping hooks are inserted into the clamping holes, and the plug of the pump base is inserted into the sealed socket. The clamping hooks slide, guided by their front inclined plates, into the clamping holes, and thus being engaged with the flange structures 1111 of the clamping holes. Therefore, the pump base 12 and the controller 11 are tightly combined. Two O-shaped sealing rings on the plug of the top shell of the pump base and the sealed socket also fit tightly. When the button is pressed, the pump base 12 is disengaged from the controller 11. The groove configured to arrange the connector 13 is set in the sealed socket of the controller 11. When the plug of the pump base is inserted into the sealed socket, the plug of the main frame is inserted into the connector 13, realizing electrical connection between the connector 13 and the pump base 12. An O-shaped sealing ring is set on a surface on which the connector 13 is attached with the shell of the controller 11. The O-shaped sealing rings on the plug of the top shell of the pump base and the O-shaped sealing ring in the sealed socket achieve sealing effect and waterproof, when the controller 11 is combined with the pump base 12.

Figure 12:
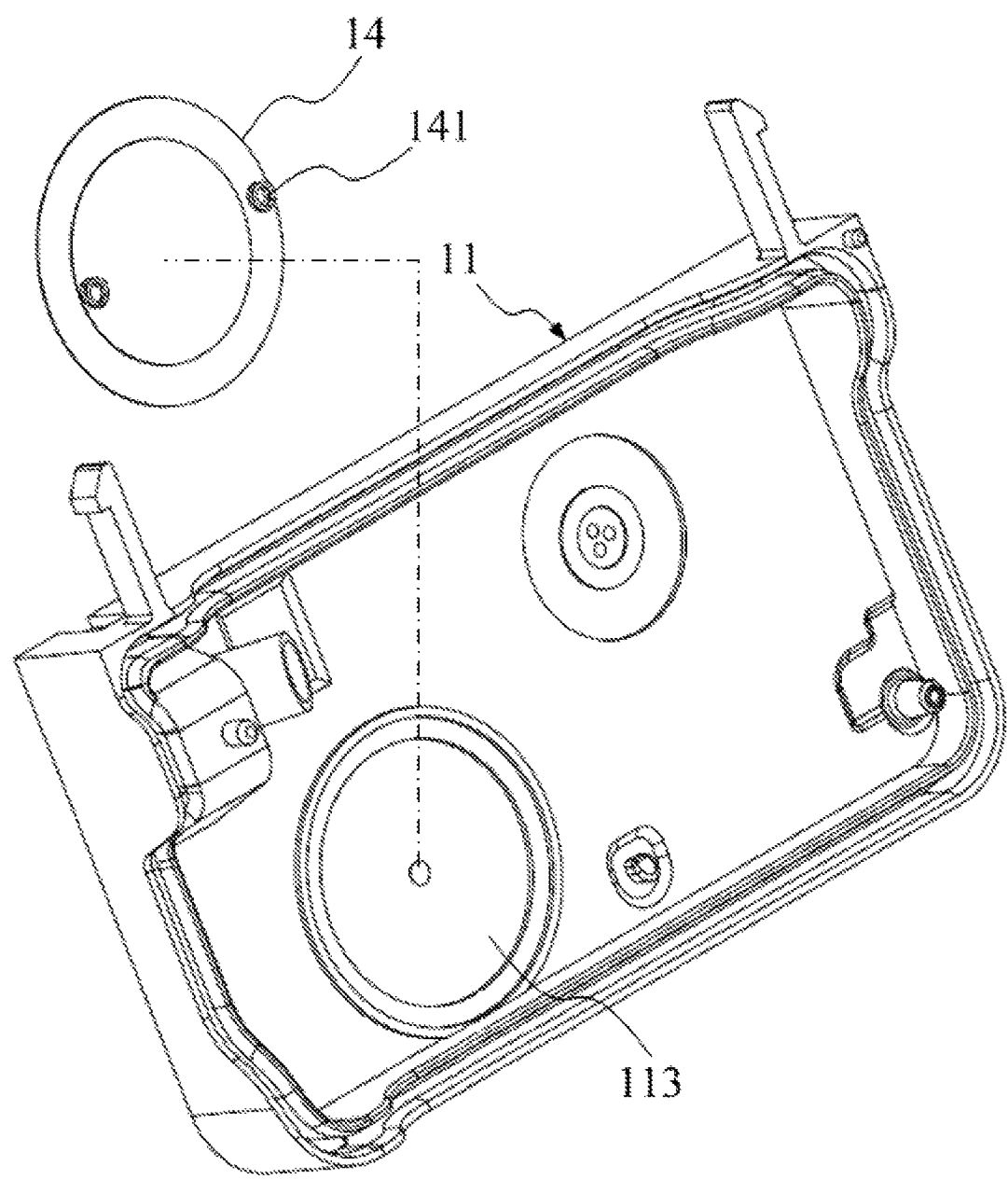
FIG. 12 schematically illustrates an exploded view of a buzzer set in the second housing according to one embodiment of the present disclosure.
Figure 13:
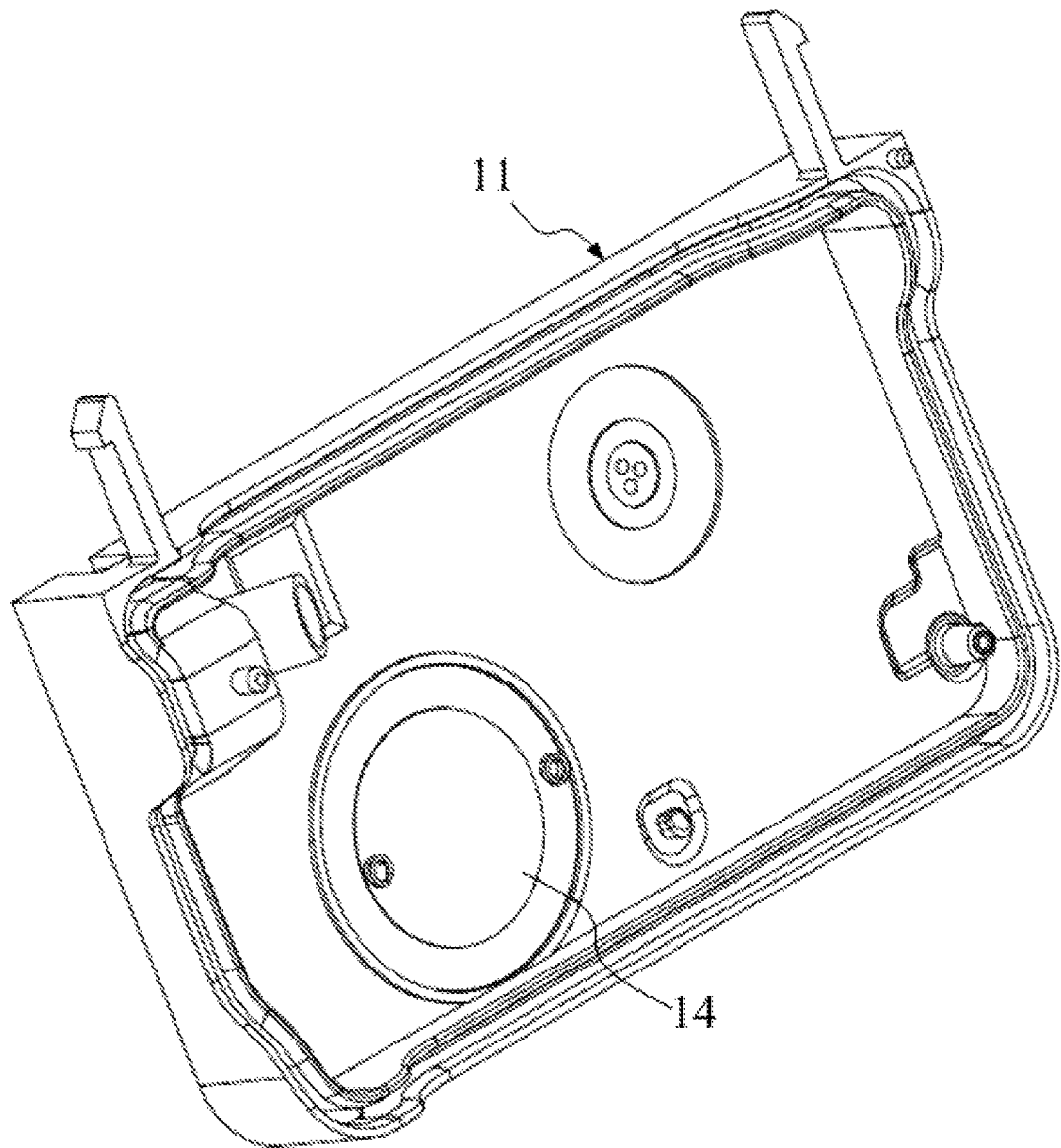
FIG. 13 schematically illustrates an combined view of a buzzer set in the second housing according to one embodiment of the present disclosure.

Referring to FIG. 12 and FIG. 13, FIG. 12 schematically illustrates an exploded view of a buzzer set in the second housing according to one embodiment of the present disclosure, and FIG. 13 schematically illustrates a buzzer set in the second housing according to one embodiment of the present disclosure. As shown in FIG. 12 and FIG. 13, the second housing is provided with a second buzzer chamber 113, in which a second buzzer 14 is disposed. And the second buzzer 14 is connected to the 3D printed circuit of the pump base via a contact 141. When the fluid stored in the pump base 12 runs out, or the device breaks down, the controller 11 will remind the user by using the second buzzer 14 to remove and discard the pump base 12, and to install a new pump base 12 and stick the tubeless fluid delivery device to the skin for sequential using.

To prevent interference between the shell of the pump base 12 and the main frame 124 in the installing process, the plug of the main frame 124 is a wedge. As shown in FIG. 12 and FIG. 13, the signal lines are distributed on both sides of the plug of the main frame 124, which realize functions of position detection, left in place detection, right in place detection, battery positive electrode, buzz positive, left side drive, right side drive and battery negative electrode. Optionally, the signal lines near the side of the delivery fluid inlet successively realize functions of buzz positive, left side drive, right left drive and battery negative electrode from top to bottom. The signal lines in the other side successively realize functions of position detection, left in place detection, right in place detection, and battery positive electrode.

Figure 14:
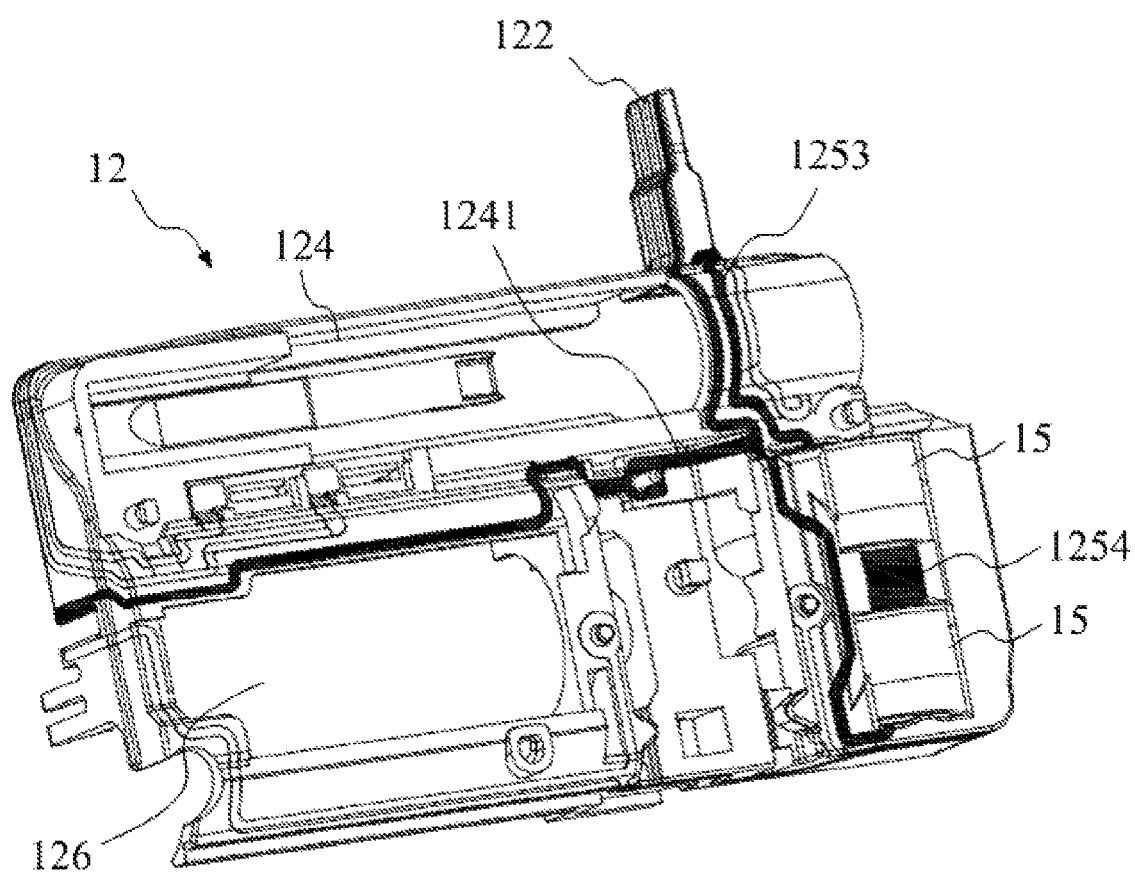
FIG. 14 schematically illustrates an internal view of a second housing according to another embodiment of the present disclosure.

Referring to FIG. 14, an internal view of a second housing according to another embodiment of the present disclosure is schematically illustrated. The distribution of the main frame 124 embedded in the pump base 12 and the ground wire is illustrated in FIG. 14. In the embodiment, the battery is configured as two button batteries 15 which are set in a battery slot 125 set on the main frame 124 and are connected via a conduction connector 1254. And the two batteries supply power through the ground wire 1241 on the main frame 124 and the battery positive electrode 1253. The ground wire is connected to the common ports of position detection, left in place detection, right in place detection and blockage detection, and connected to a buzz positive electrode and the battery negative electrode.

Figure 15:
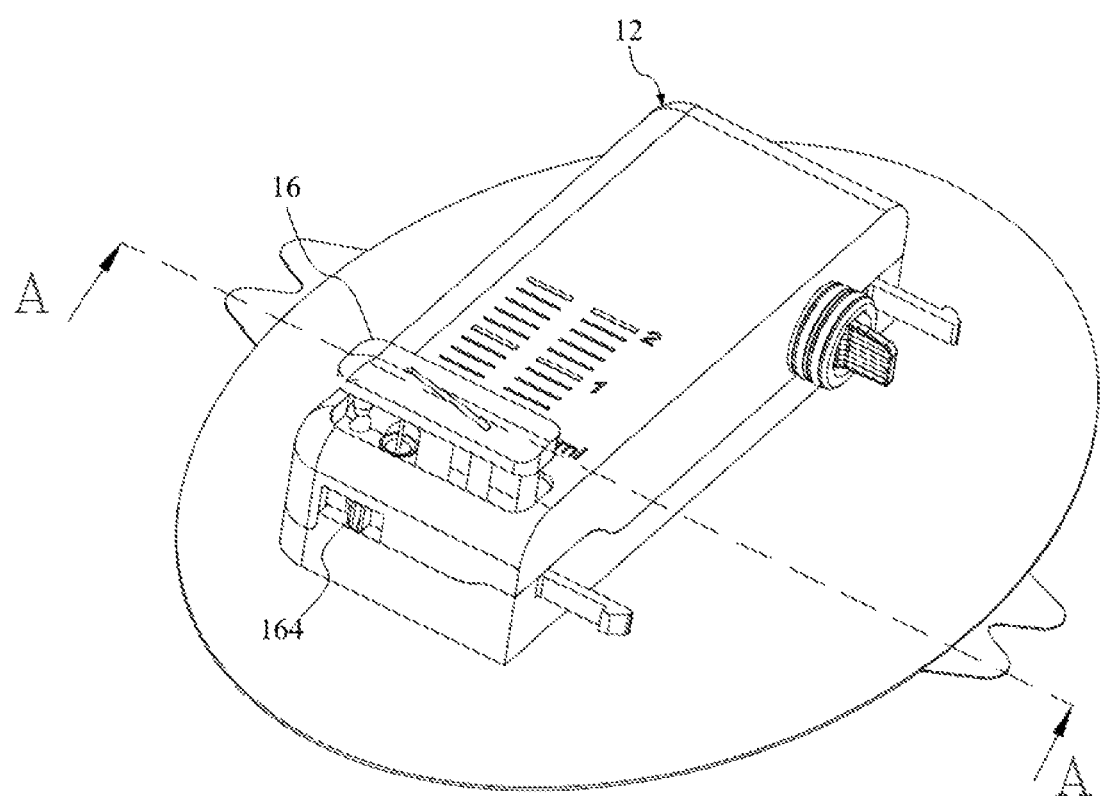
FIG. 15 schematically illustrates a subcutaneous cannula installation device according to one embodiment of the present disclosure.
Figure 16:
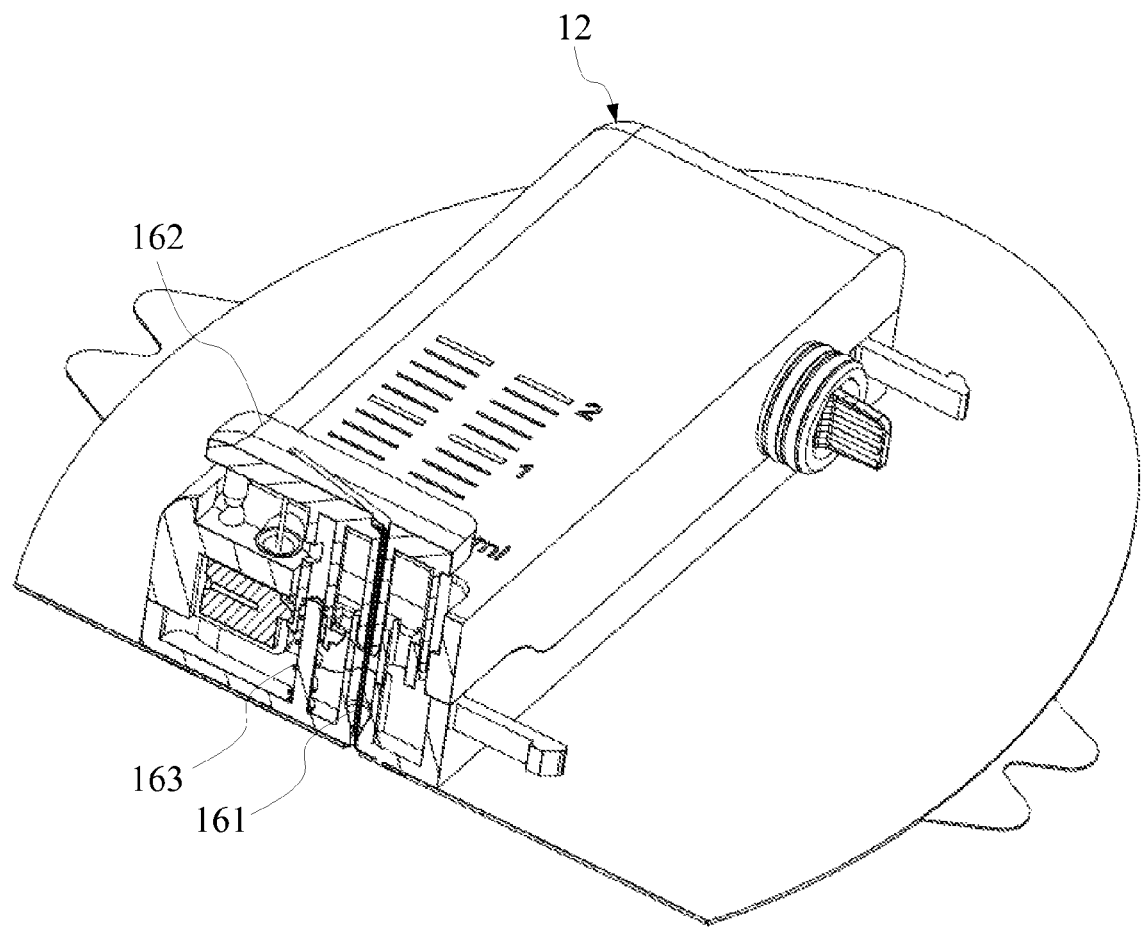
FIG. 16 schematically illustrates a sectional view along A-A direction of FIG. 15.
Figure 17:
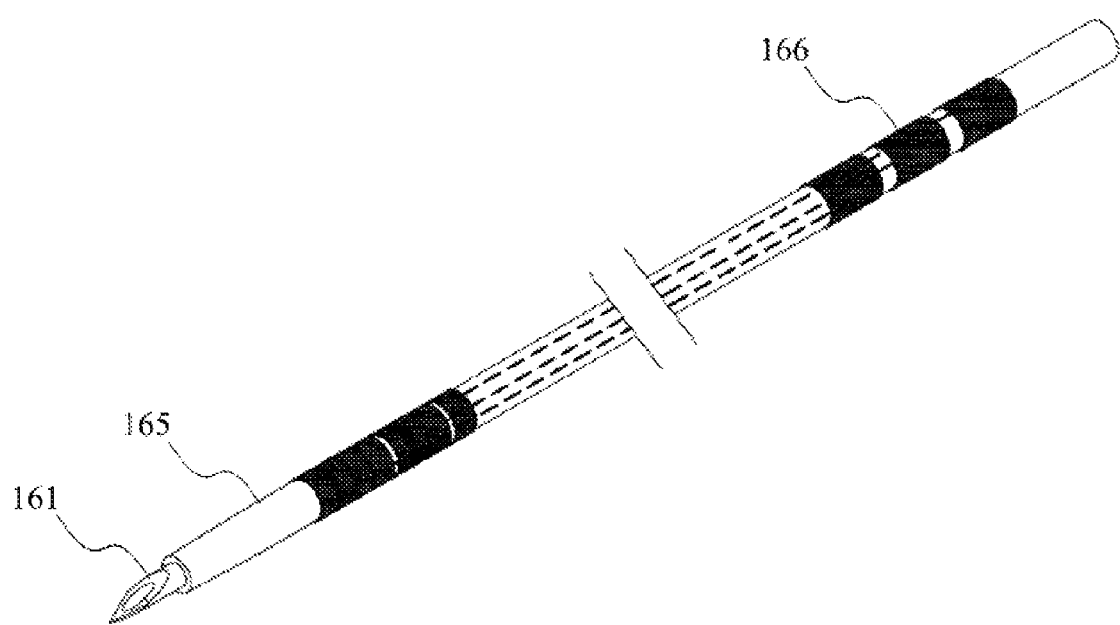
FIG. 17 schematically illustrates a steel needle, an indwelling cannula and a glucose sensor according to one embodiment of the present disclosure.

Referring to FIG. 15 to FIG. 17, FIG. 15 schematically illustrates a subcutaneous cannula installation device according to one embodiment of the present disclosure, FIG. 16 schematically illustrates a sectional view along A-A direction of FIG. 15, and FIG. 17 schematically illustrates a steel needle, an indwelling cannula and a glucose sensor according to one embodiment of the present disclosure. As shown in FIG. 15 to FIG. 17, the pump base 12 further includes a subcutaneous cannula installation device 16 having a steel needle 161, a steel needle bed 162, a spring 163 and a toggle switch 164. The pump base 12 further includes an indwelling cannula 165 of the steel needle 161, and the indwelling cannula 165 is implanted subcutaneously via the aid of the steel needle 161. In one embodiment, the steel needle is a hollow needle, and the indwelling cannula covers the hollow needle. In one embodiment, the steel needle is a groove steel needle, and the indwelling cannula is set in the groove of the groove steel needle. Referring to FIG. 17, a glucose sensor 166 is set on the outer surface of the indwelling cannula.

In the embodiment, the steel needle is a hollow needle or a groove steel needle. When the steel needle is a hollow needle, the indwelling cannula covers the hollow needle, which is shown in FIG. 17. When the steel needle is a groove steel needle, the indwelling cannula is set in the groove of the groove steel needle, which is not shown.

In one embodiment, as shown in FIG. 15 to FIG. 17, in the tubeless fluid delivery device, a fluid stored in a reservoir (not shown, the reservoir is set in the slot for reservoir) in the pump base 12 is infused into a patient's body through the indwelling cannula or the steel needle embedded subcutaneously. The indwelling cannula and/or the steel needle are both embedded subcutaneously via the subcutaneous cannula installation device 16. From a structural standpoint, the subcutaneous cannula installation device 16 includes the steel needle 161, the steel needle bed 162, the spring 163 and the toggle switch 164. From a functional standpoint, the subcutaneous cannula installation device 16 includes an ejection mechanism, a return needle device, or a combination thereof, where the ejection mechanism may be automatic or a manual, and the return needle device may be automatic or a manual. When the steel needle is implanted, the subcutaneous cannula installation device 16 directly punctures the steel needle into the skin of the patient via the ejection mechanism. When the indwelling cannula is implanted, the subcutaneous cannula installation device 16 uses the steel needle to puncture the skin of the patient by using the ejection mechanism, and then pulls out the steel needle by using the return needle device. The subcutaneous cannula installation device 16 may be set inside the pump base or be set out of the pump base. The inner structure of the subcutaneous cannula installation device 16 embedded in the pump base is shown in FIG. 15 and FIG. 16. Here is an example of implanting the indwelling cannula into the skin of a patient, while the steel needle is a hollow needle, and the steel needle is set in the indwelling cannula. Initially, the steel needle and the indwelling cannula are both located in the steel needle bed. When the steel needle bed is pushed down, the steel needle punctures the skin of the patient and implants the indwelling cannula into the skin of patient. When the steel needle bed is pushed to the bottom, the toggle switch limit the steel needle bed, and the spring is in the compression state. Thereafter, the toggle switch is touched to release the spring, so as to push the steel needle base to move upward. As such, the steel needle is pulled out from the body of the patient.

Because the glucose sensor and the indwelling cannula are the same in aspects such as action area on body, disposable using, aseptic production, etc., the glucose sensor may be integrated on an outer surface of the indwelling cannula. As shown in FIG. 17, the indwelling cannula and the glucose sensor are simultaneously implanted subcutaneously.

In the tubeless fluid delivery device of the present disclosure, if the glucose sensor is integrated on the outer surface of the indwelling cannula, the signal lines located on both sides of the plug of the main frame 124 realize functions of a reference electrode, a buzz left in place detection, a public right in place detection, a battery positive electrode, a working electrode, a left side drive, a right side drive and a battery negative electrode. Optionally, the signal lines near the side of the delivery fluid inlet successively realize functions of a working electrode, a left side drive, a right left drive and a battery negative electrode from top to bottom, and the signal lines in the other side successively realize functions of a reference electrode, a buzz left in place detection, a public right in place detection and a battery positive electrode. The ground wire is connected to the common ports of position detection, left in place detection, right in place detection and blockage detection, and connected to a battery negative electrode.

Figure 18:
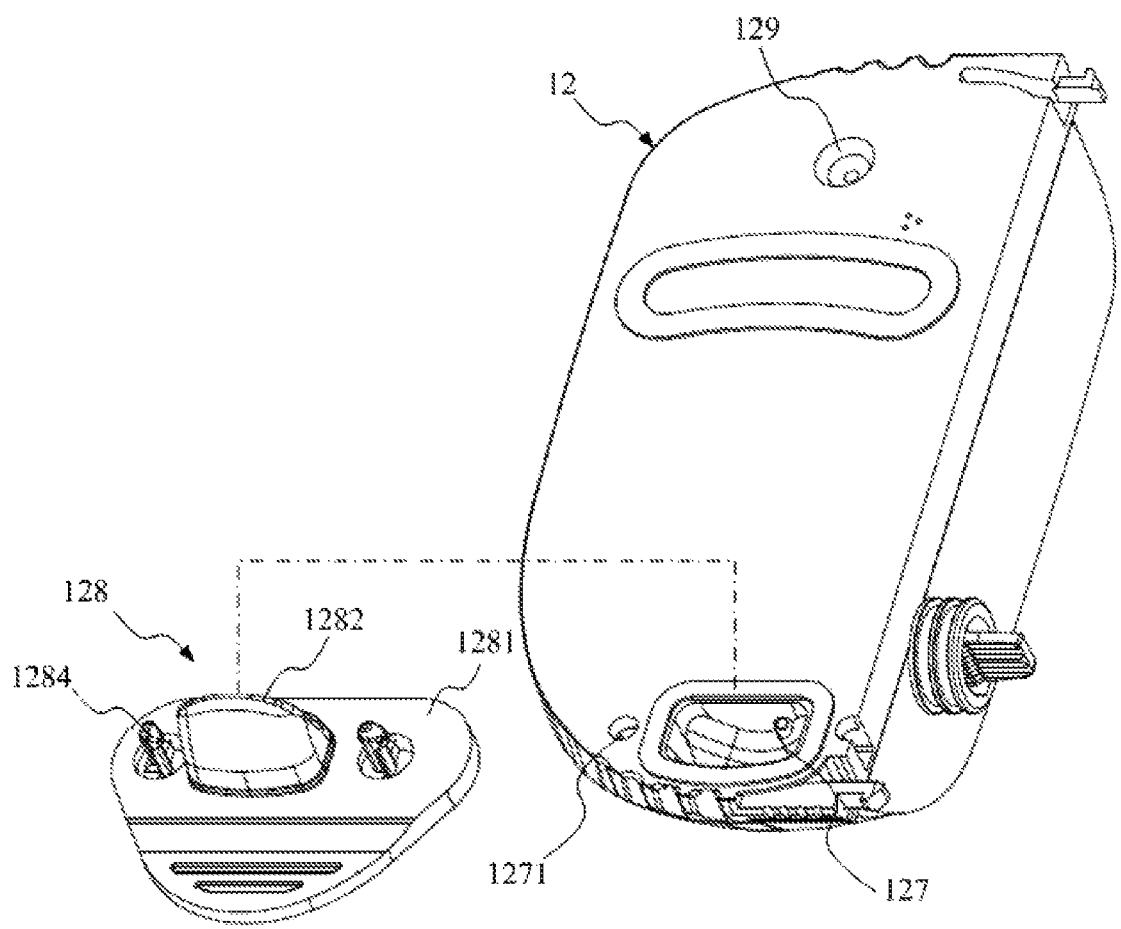
FIG. 18 schematically illustrates an exploded view of a delivery fluid plug according to one embodiment of the present disclosure.
Figure 19:
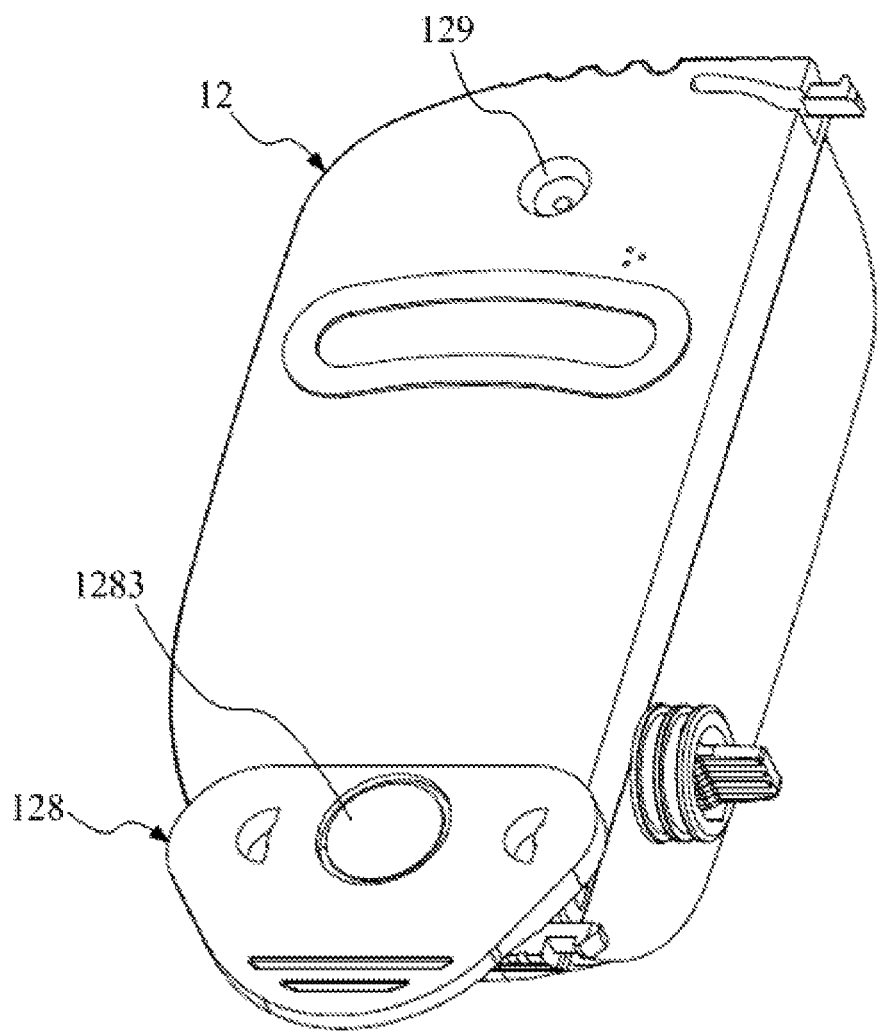
FIG. 19 schematically illustrates a delivery fluid plug according to one embodiment of the present disclosure.

Referring to FIG. 18 and FIG. 19, FIG. 18 schematically illustrates an exploded view of a delivery fluid plug according to one embodiment of the present disclosure, and FIG. 19 schematically illustrates a delivery fluid plug according to one embodiment of the present disclosure. As shown in FIG. 18 and FIG. 19, the pump base 12 further includes a fluid outlet 127, which is provided with a delivery fluid plug 128 having a plastic base 1281, a silica gel plug 1282 and a polymer film 1283. The delivery fluid plug 128 is connected to the second housing via a fastener (an engagement structure having a clamping hook 1284 and a clamping hole 1271 shown in FIG. 18). The delivery fluid plug 128 can be disengaged from the pump base 12, when the plastic base 1281 is lifted. In one embodiment, when the tubeless fluid delivery device in the present disclosure infuses the fluid into the body of the patient, a syringe is needed to infuse the fluid into the pump base through the delivery fluid inlet. To prevent the fluid leakage in the delivery process, a delivery fluid plug is set in the fluid outlet of the pump base. As shown in FIG. 18, the delivery fluid plug 128 includes the plastic base 1281, the silica gel plug 1282 and the polymer film 1283. The delivery fluid plug 128 is connected to the bottom shell of the pump base by a clamping hook of the plastic base 1281, and the delivery fluid plug prevents leakage of the fluid around. The polymer film 1283 realizes a ventilation function and a waterproof function. The delivery fluid plug 128 can be disengaged from the pump base, when the plastic base is lifted. The reference sign 129 in FIG. 18 and FIG. 19 indicates the delivery fluid inlet.

Figure 20:
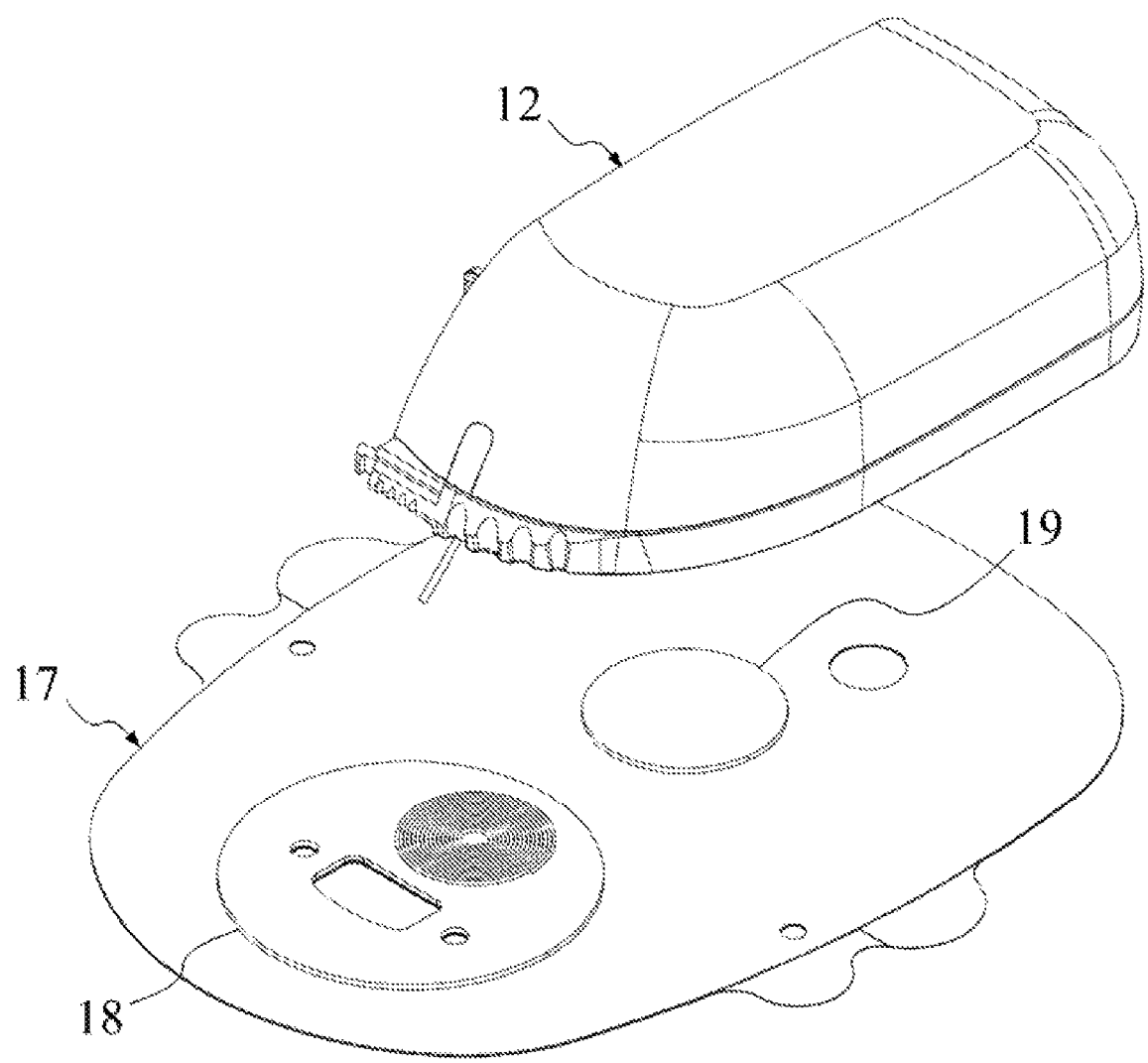
FIG. 20 schematically illustrates a medical adhesive tape, a skin heating device and an identity recognition tag according to one embodiment of the present disclosure.

Referring to FIG. 20, a medical adhesive tape, a skin heating device and an identity recognition tag according to one embodiment of the present disclosure are schematically illustrated. As shown in FIG. 20, the pump base 12 includes a medical adhesive tape 17 configured to be stuck to the skin of the patient. The tubeless fluid delivery device further includes a skin heating device 18 configured to heat the skin at which the fluid is infused. The pump base further includes an identity recognition tag 19, which may be a near field communication (NFC) tag, a radio frequency identification (RFID) tag or an identity recognition chip.

In some embodiments, the tubeless fluid delivery device is stuck to the skin of the patient by the medical adhesive tape 17. The pump base 12 is bigger and heavier than the controller 11. It only needs to pre-fix the medical adhesive tape 17 on the bottom shell of the pump base, such that the tubeless fluid delivery device can be stably attached to the patient. When the pump base 12 is removed and replaced, the medical adhesive tape 17 is also removed and replaced together. The position at which the new pump base 12 is stuck may be changed, so as to avoid the physical discomfort of the patient caused by sticking the medical adhesive tape at the same position for a long time and repeated punctures. The skin heating device 18, the identity recognition tag 19, or a combination thereof, is set between the medical adhesive tape and the bottom shell of the pump base. When the patient is infused with the insulin, the skin heating device 18 may reduce the delay of the insulin peak action time. The identity recognition tag 19 is configured to store the personalized information of the pump base 12 and recognize identity, which may be a near field communication (NFC) tag, a radio frequency identification (RFID) tag or an identity recognition chip.

In summary, the tubeless fluid delivery device in the present disclosure uses separable structure to reduce costs. It uses the active controller as a main control machine, and uses the pump base as passive consumables. That is, the active part can be reused, while the passive part is disposable. The two parts are packed separately and can be used together to treat the patient. Specifically, when a tubeless fluid delivery device is needed, the patient assembles the controller and pump base together to form the delivery device, sticks the formed tubeless fluid delivery device to his/her skin and then uses it as normal. When the fluid stored in the pump base runs out, or the device breaks down, the controller will remind the user, by using the buzzer, to remove and discard the pump base. The controller further reminds the user to install a new pump base to the controller to form a new tubeless fluid delivery device, and stick the tubeless fluid delivery device to the skin for sequential using. The present disclosure overcomes the various shortcomings of the current technology and has high industrial utilization values.

Although the present disclosure has been disclosed as above with reference to preferred embodiments thereof but will not be limited thereto. Those skilled in the art can modify and vary the embodiments without departing from the spirit and scope of the present disclosure. Accordingly, without departing from the scope of the present invented technology scheme, whatever simple modification and equivalent variation belong to the protection range of the present invented technology scheme.

What is claimed is:

1. A tubeless fluid delivery device, comprising:
   a controller, comprising a first housing which has a first built-in circuit, wherein the first housing is provided with a first engagement part and a first insertion part electrically connected to the first built-in circuit; and
   a pump base combined with the controller, which comprises a second housing having a second built-in circuit, a reservoir, a piston, a push rod, a driving member and a battery, wherein the second housing is provided with a second engagement part correspondingly engaged with the first engagement part and a second insertion part electrically connected to the second built-in circuit, wherein the second insertion part is correspondingly inserted in the first insertion part to realize electrical connection between the first built-in circuit and the second built-in circuit.

2. The tubeless fluid delivery device according to claim 1, wherein the first engagement part is a clamping hole or a clamping slot.

3. The tubeless fluid delivery device according to claim 2, wherein the second engagement part is a clamping hook corresponding to the clamping hole or the clamping slot, and the clamping hook is connected to a clamping hook handle, wherein the clamping hook is engaged with the clamping hole or the clamping slot, or disengaged from the clamping hole or the clamping slot by controlling the clamping hook handle.

4. The tubeless fluid delivery device according to claim 2, wherein the second engagement part is a clamping hook corresponding to the clamping hole or the clamping slot, and the first housing is provided with a button configured to separate the clamping hook from the clamping hole or the clamping slot.

5. The tubeless fluid delivery device according to claim 1, wherein the first insertion part is a sealed socket, the sealed socket is provided with a groove in which a connector configured to be electrically connected to the first built-in circuit is disposed, wherein an O-shaped sealing ring is set on a surface on which the connector is attached with the sealed socket.

6. The tubeless fluid delivery device according to claim 5, wherein the second insertion part is a plug which comprises a plug body circumferentially set with an O-shaped sealing ring and a bolt embedded in the plug body, wherein when the plug is inserted into the sealed socket, the bolt is inserted into the connector and electrically connected to the connector, wherein the O-shaped sealing ring on the plug body and the sealed socket fit tightly to achieve waterproof sealing.

7. The tubeless fluid delivery device according to claim 1, wherein a main frame used as a structure supporter and a supporter for the second built-in circuit is embedded in the pump body, and the second built-in circuit set on the main frame is a 3D printed circuit which is electrically connected to the second insertion part.

8. The tubeless fluid delivery device according to claim 7, wherein signal lines on the second insertion part realizes a first combination of functions comprising a position detection, a left in place detection, a right in place detection, a battery positive electrode, a blockage detection, a left side drive, a right side drive and a battery negative electrode; or a second combination of functions comprising a reference electrode, a buzz left in place detection, a public right in place detection, a battery positive electrode, a working electrode, a left side drive, a right side drive and a battery negative electrode; or a third combination of functions comprising a position detection, a left in place detection, a right in place detection, a battery positive electrode, a buzz positive, a left side drive, a right side drive and a battery negative electrode.

9. The tubeless fluid delivery device according to claim 8, wherein if the first combination or the second combination is used, a ground wire of the second insertion part is connected to a common port of the position detection, a common port of the left in place detection, a common port of the right in place detection, a common port of the blockage detection, and the battery negative electrode; if the third combination is used, the ground wire of the second insertion part is connected to the common port of the position detection, the common port of the left in place detection, the common port of the right in place detection, the common port of the blockage detection, the buzz positive electrode, and the battery negative electrode.

10. The tubeless fluid delivery device according to claim 1, wherein the first built-in circuit of the controller comprises a control circuit and a processor.

11. The tubeless fluid delivery device according to claim 1, wherein the first housing is provided with a first buzzer chamber in which a first buzzer is disposed, and the first buzzer is connected to the first built-in circuit of the controller via a wire; or the second housing is provided with a second buzzer chamber in which a second buzzer is disposed, and the second buzzer is connected to the second built-in circuit of the controller via a contact.

12. The tubeless fluid delivery device according to claim 1, wherein the pump base further comprises a subcutaneous cannula installation device having a steel needle, a steel needle bed, a spring and a toggle switch.

13. The tubeless fluid delivery device according to claim 12, wherein the pump base further comprises an cannula combined with the steel needle, and the cannula is implanted subcutaneously via the aid of the steel needle.

14. The tubeless fluid delivery device according to claim 13, wherein the steel needle is a hollow needle, and the cannula covers the hollow needle; or the steel needle is a groove steel needle, the cannula is set in the groove of the groove steel needle.

15. The tubeless fluid delivery device according to claim 12, wherein a glucose sensor is set on an outer surface of the cannula.

16. The tubeless fluid delivery device according to claim 1, wherein the pump base further comprises a fluid outlet on which an delivery fluid plug having a plastic base, a silica gel plug and a polymer film is provided, the delivery fluid plug is connected to the second housing via a fastener, when the plastic base is lifted, the delivery fluid plug is detachable from the pump base.

17. The tubeless fluid delivery device according to claim 1, wherein a medical adhesive tape used to be stuck to the skin of a patient is fixed on the pump base.

18. The tubeless fluid delivery device according to claim 1, wherein the tubeless fluid delivery device further comprises a skin heating device configured to heat the skin at which the fluid is infused.

19. The tubeless fluid delivery device according to claim 1, wherein the pump base further comprises an identity recognition tag, and the identity recognition tag is a near field communication (NFC) tag, a radio frequency identification (RFID) tag or an identity recognition chip.

\* \* \* \* \*